(12) United States Patent
Carter et al.

(10) Patent No.: US 10,357,249 B2
(45) Date of Patent: Jul. 23, 2019

(54) SURGICAL STAPLING APPARATUS INCLUDING RELEASABLE SURGICAL BUTTRESS

(71) Applicant: Covidien LP, Mansfield, MA (US)

(72) Inventors: Sally Carter, Nashua, CT (US); Gerald Hodgkinson, Guilford, CT (US); Richard Stevenson, Colchester, CT (US); Arthur Hislop, Plantsville, CT (US); Ernest Aranyi, Easton, CT (US); Jennifer (Whiffen) Diederich, Eagle River, AK (US)

(73) Assignee: Covidien LP, Mansfield, MA (US)

( * ) Notice: Subject to any disclaimer, the term of this patent is extended or adjusted under 35 U.S.C. 154(b) by 467 days.

(21) Appl. No.: 15/168,924

(22) Filed: May 31, 2016

(65) Prior Publication Data

US 2016/0270793 A1    Sep. 22, 2016

Related U.S. Application Data

(62) Division of application No. 13/325,481, filed on Dec. 14, 2011, now Pat. No. 9,351,731.

(51) Int. Cl.
*A61B 17/115* (2006.01)
*A61B 17/10* (2006.01)
(Continued)

(52) U.S. Cl.
CPC ...... *A61B 17/07292* (2013.01); *A61B 17/068* (2013.01); *A61B 17/072* (2013.01);
(Continued)

(58) Field of Classification Search
CPC .................. A61B 17/1155; A61B 17/07292
See application file for complete search history.

(56) References Cited

U.S. PATENT DOCUMENTS

| 3,054,406 A | 9/1962 | Usher |
| 3,079,606 A | 3/1963 | Bobrov et al. |

(Continued)

FOREIGN PATENT DOCUMENTS

| AU | 2012201677 A1 | 11/2012 |
| AU | 2013200367 A1 | 9/2013 |

(Continued)

OTHER PUBLICATIONS

European Office Action corresponding to counterpart European Patent Application No. EP 13 19 7958.5 dated Dec. 11, 2017.

(Continued)

*Primary Examiner* — Stephen F. Gerrity
*Assistant Examiner* — Joshua G Kotis

(57) ABSTRACT

A staple cartridge for use with a surgical stapling apparatus includes a cartridge body including a tissue contacting surface defining a plurality of staple retaining slots, a staple disposed within each staple retaining slot of the cartridge body, and a substantially circular buttress. The buttress includes an inner portion, an outer portion, and a middle portion extending between the inner portion and the outer portion. At least one stiffened region joins the buttress to the tissue contacting surface of the cartridge body. The inner portion, the middle portion, the outer portion, and the at least one stiffened region are all formed from a common material.

18 Claims, 7 Drawing Sheets

(51) Int. Cl.
*A61B 17/068* (2006.01)
*A61B 17/072* (2006.01)
*A61B 17/00* (2006.01)

(52) U.S. Cl.
CPC ...... *A61B 17/07207* (2013.01); *A61B 17/105* (2013.01); *A61B 17/1155* (2013.01); *A61B 2017/00831* (2013.01)

(56) References Cited

U.S. PATENT DOCUMENTS

| | | | |
|---|---|---|---|
| 3,124,136 A | 3/1964 | Usher | |
| 3,364,200 A | 1/1968 | Ashton et al. | |
| 3,490,675 A | 1/1970 | Green et al. | |
| 3,499,591 A | 3/1970 | Green | |
| 3,797,494 A | 3/1974 | Zaffaroni | |
| 3,939,068 A | 2/1976 | Wendt et al. | |
| 3,948,666 A | 4/1976 | Kitanishi et al. | |
| 3,953,566 A * | 4/1976 | Gore .................. | B01D 71/36 264/505 |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |
| 4,416,698 A | 11/1983 | McCorsley, III | |
| 4,429,695 A | 2/1984 | Green | |
| 4,452,245 A | 6/1984 | Usher | |
| 4,473,670 A | 9/1984 | Kessidis | |
| 4,605,730 A | 8/1986 | Shalaby et al. | |
| 4,626,253 A | 12/1986 | Broadnax, Jr. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,024,841 A * | 6/1991 | Chu .................. | A61K 38/39 128/DIG. 8 |
| 5,040,715 A | 8/1991 | Green et al. | |
| 5,057,334 A | 10/1991 | Vail | |
| 5,065,929 A | 11/1991 | Schulze et al. | |
| 5,112,496 A | 5/1992 | Dhawan et al. | |
| 5,162,430 A | 11/1992 | Rhee et al. | |
| 5,205,459 A | 4/1993 | Brinkerhoff et al. | |
| 5,263,269 A | 11/1993 | Tjarnlund | |
| 5,263,629 A | 11/1993 | Trumbull et al. | |
| 5,281,197 A | 1/1994 | Arias et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,713,920 A | 2/1998 | Bezwada et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A | 11/1998 | Yoon | |
| 5,843,096 A | 12/1998 | Igaki et al. | |
| 5,871,135 A | 2/1999 | Williamson, IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,957,363 A | 9/1999 | Heck | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,330,965 B1 | 12/2001 | Milliman et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 | 1/2003 | Grant et al. | |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,568,398 B2 | 5/2003 | Cohen | |
| 6,590,095 B1 | 7/2003 | Schleicher et al. | |
| 6,592,597 B2 | 7/2003 | Grant et al. | |
| 6,605,294 B2 | 8/2003 | Sawhney | |
| 6,610,006 B1 | 8/2003 | Amid et al. | |
| 6,627,749 B1 | 9/2003 | Kumar | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,656,200 B2 | 12/2003 | Li et al. | |

(56) References Cited

U.S. PATENT DOCUMENTS

| | | |
|---|---|---|
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,334,717 B2 | 2/2008 | Rethy et al. |
| 7,334,828 B2 | 2/2008 | Budde et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |

(56) References Cited

U.S. PATENT DOCUMENTS

| | | |
|---|---|---|
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0092912 A1 | 5/2004 | Jinno et al. |
| 2004/0093029 A1 | 5/2004 | Zubik et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0143756 A1 | 6/2005 | Jankowski |
| 2005/0149073 A1 | 7/2005 | Arani et al. |
| 2005/0154093 A1 | 7/2005 | Kwon et al. |
| 2005/0228446 A1 | 10/2005 | Mooradian et al. |
| 2005/0245965 A1 | 11/2005 | Orban, III et al. |
| 2005/0283256 A1 | 12/2005 | Sommerich et al. |
| 2006/0004407 A1 | 1/2006 | Hiles et al. |
| 2006/0008505 A1 | 1/2006 | Brandon |
| 2006/0025816 A1 | 2/2006 | Shelton |
| 2006/0085030 A1 | 4/2006 | Bettuchi et al. |
| 2006/0093672 A1 | 5/2006 | Kumar et al. |
| 2006/0111738 A1 | 5/2006 | Wenchell |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0027550 A1* | 2/2007 | Farnsworth ........... A61L 31/146 623/23.71 |
| 2007/0027552 A1* | 2/2007 | Farnsworth ........... A61L 31/146 623/23.74 |
| 2007/0034669 A1 | 2/2007 | de la Torre et al. |

(56) References Cited

U.S. PATENT DOCUMENTS

| | | |
|---|---|---|
| 2007/0049953 A2 | 3/2007 | Shimoji et al. |
| 2007/0054880 A1 | 3/2007 | Saferstein et al. |
| 2007/0114262 A1 | 5/2007 | Mastri et al. |
| 2007/0123839 A1 | 5/2007 | Rousseau et al. |
| 2007/0175961 A1 | 8/2007 | Shelton et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0243227 A1 | 10/2007 | Gertner |
| 2007/0246505 A1 | 10/2007 | Pace-Floridia et al. |
| 2007/0297987 A1* | 12/2007 | Stad ............... A61B 17/0642 424/9.4 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1* | 3/2009 | Bell ............... A61B 17/07207 606/75 |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0016872 A1* | 1/2010 | Bayon ............... A61F 2/0063 606/151 |
| 2010/0016888 A1* | 1/2010 | Calabrese ......... A61B 17/072 606/219 |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0278891 A1* | 11/2010 | Ringeisen ............... A61B 17/80 424/422 |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0089375 A1 | 4/2011 | Chan et al. |
| 2011/0125138 A1 | 5/2011 | Malinouskas et al. |
| 2011/0166673 A1 | 7/2011 | Patel et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2011/0282446 A1 | 11/2011 | Schulte et al. |
| 2011/0293690 A1 | 12/2011 | Griffin et al. |
| 2012/0035629 A1* | 2/2012 | Sherwinter ......... A61B 17/0057 606/153 |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0241499 A1 | 9/2012 | Baxter, III et al. |
| 2012/0253298 A1 | 10/2012 | Henderson et al. |
| 2012/0273547 A1 | 11/2012 | Hodgkinson et al. |
| 2013/0037596 A1 | 2/2013 | Bear et al. |
| 2013/0105548 A1* | 5/2013 | Hodgkinson ......... A61B 17/072 227/176.1 |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0123816 A1 | 5/2013 | Hodgkinson et al. |
| 2013/0146641 A1 | 6/2013 | Shelton, IV et al. |
| 2013/0153633 A1 | 6/2013 | Casasanta, Jr. et al. |
| 2013/0153634 A1* | 6/2013 | Carter ............... A61B 17/072 227/176.1 |
| 2013/0153635 A1 | 6/2013 | Hodgkinson |
| 2013/0153636 A1 | 6/2013 | Shelton, IV et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | (Tarinelli) Racenet et al. |
| 2013/0193190 A1* | 8/2013 | Carter ............... A61B 17/07292 227/179.1 |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |

(56) References Cited

U.S. PATENT DOCUMENTS

| | | |
|---|---|---|
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |

FOREIGN PATENT DOCUMENTS

| | | |
|---|---|---|
| CA | 2 667 434 A1 | 5/2008 |
| CN | 1301685 C | 2/2007 |
| CN | 101310680 A | 11/2008 |
| CN | 101332110 A | 12/2008 |
| DE | 1602563 U | 3/1950 |
| DE | 19924311 A1 | 11/2000 |
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 A1 | 8/2009 |
| EP | 2 090 244 A2 | 8/2009 |
| EP | 2 090 252 A2 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 A1 | 10/2010 |
| EP | 2 258 282 A2 | 12/2010 |
| EP | 2 292 276 A2 | 3/2011 |
| EP | 2 311 386 A2 | 4/2011 |
| EP | 2 436 348 A1 | 4/2012 |
| EP | 2 462 880 A2 | 6/2012 |
| EP | 2491867 A1 | 8/2012 |
| EP | 2 497 431 A1 | 9/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 6-54857 | 3/1994 |
| JP | 07-124166 A | 5/1995 |
| JP | 2000-166933 A | 6/2000 |
| JP | 2002-202213 A | 7/2002 |
| JP | 2002-369820 A | 12/2002 |
| JP | 2005-508796 A | 4/2005 |
| JP | 2007-505708 A | 3/2007 |
| JP | 2007-124166 A | 5/2007 |
| JP | 2008528203 A | 7/2008 |
| JP | 2009189846 A | 8/2009 |
| JP | 2010-528821 A | 8/2010 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 98/38923 A1 | 9/1998 |
| WO | 99/45849 A1 | 9/1999 |
| WO | 03/082126 A1 | 10/2003 |
| WO | 03/088845 A2 | 10/2003 |
| WO | 03/094743 A1 | 11/2003 |
| WO | 03/105698 A1 | 12/2003 |
| WO | 2005079675 A2 | 9/2005 |
| WO | 2006/023578 A2 | 3/2006 |
| WO | 2006044490 A2 | 4/2006 |
| WO | 2006083748 A1 | 8/2006 |
| WO | 2007/121579 A1 | 11/2007 |
| WO | 2008/057281 A2 | 5/2008 |

(56) References Cited

FOREIGN PATENT DOCUMENTS

| WO | 2008/109125 A1 | 9/2008 |
|---|---|---|
| WO | 2008/157172 A1 | 12/2008 |
| WO | 2010/075298 A2 | 7/2010 |
| WO | 2011143183 A2 | 11/2011 |
| WO | 2012044848 A1 | 4/2012 |

OTHER PUBLICATIONS

Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
"What is Ultrasonic Welding?", http://www.dukane.com/us/PPL.sub.--whatisUPA.htm, Mar. 14, 2010.
International Search Report corresponding to European Application No. EP 05 02 2585.3, completed on Jan. 25, 2006 and dated Feb. 3, 2006; 4 pages.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012;(7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012;(8 pp).
European Search Report corresponding to EP 12 15 8861.0, completed Jul. 17, 2012 and dated Jul. 24, 2012;(9 pp).
European Search Report corresponding to EP 12 16 5878.5, completed Jul. 24, 2012 and dated Aug. 6, 2012;(8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013I; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014;(9 pp).
Extended European Search Report corresponding to EP 13 19 7958.5, completed Apr. 4, 2014 and dated Apr. 15, 2014;(8 pp).
Extended European Search Report corresponding to EP 13 19 4995.0, completed Jun. 5, 2014 and dated Jun. 16, 2014;(5 pp).
Extended European Search Report corresponding to EP 14 15 7195.0, completed Jun. 5, 2014 and dated Jun. 18, 2014;(9 pp).
Extended European Search Report corresponding to EP 14 15 6342.9, completed Jul. 22, 2014 and dated Jul. 29, 2014;(8 pp).
Extended European Search Report corresponding to EP 14 16 9739.1, completed Aug. 19, 2014 and Aug. 29, 2014;(7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).

(56) References Cited

OTHER PUBLICATIONS

Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln. No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Canadian Office Action corresponding to counterpart Int'l Appln. No. CA 2,665,206 dated Nov. 19, 2013.
Chinese Notification of Reexamination corresponding to counterpart Int'l Appln. No. CN 201010517292.8 dated Jun. 2, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Japanese Notice of Allowance corresponding to counterpart Patent Appln. JP 2013-250857 dated Apr. 2, 2018.
Japanese Office Action corresponding to counterpart Int'l Appln. No. JP 2013-154561 dated May 23, 2017.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Chinese Second Office Action corresponding to counterpart Int'l Appln. No. CN 201310353628.5 dated Sep. 26, 2016.
Chinese First Office Action corresponding to counterpart Int'l Appln. No. CN 2013107068710 dated Dec. 16, 2016.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Australian Examination Report No. 1 corresponding to counterpart Int'l Appln. AU 2012244382 dated Jul. 10, 2016.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.

(56) References Cited

OTHER PUBLICATIONS

Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Japanese Office Action corresponding to counterpart Int'l Appln. No. JP 2013-250857 dated Aug. 17, 2017.
Japanese Office Action corresponding to counterpart Japanese Patent Appln. No. JP 2013-154561 dated Jan. 15, 2018.
European Office Action corresponding to counterpart European Appln. No. EP 15 17 4146.9 dated May 15, 2017.
Japanese Office Action corresponding to counterpart Japanese Appln. No. JP 2013-154561 dated May 23, 2017.
European Office Action corresponding to counterpart European Appln. No. EP 12 19 4784.0 dated May 29, 2017.
Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.
Australian Examination Report No. 1 corresponding to counterpart Australian Appln. No. AU 2014200793 dated Sep. 2, 2017.
Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.
Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 79585 dated Dec. 11, 2017.
Australian Examination Report No. 1 corresponding to counterpart Int'l Appln. No. AU 2013266989 dated Jul. 10, 2017.

* cited by examiner

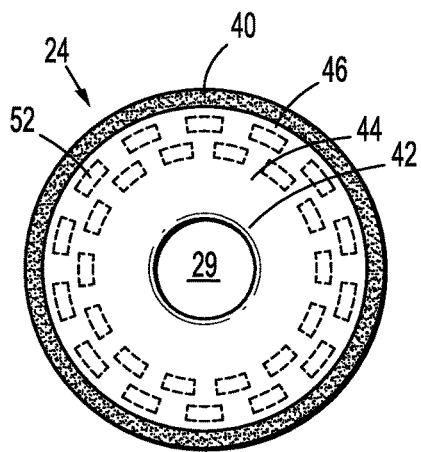
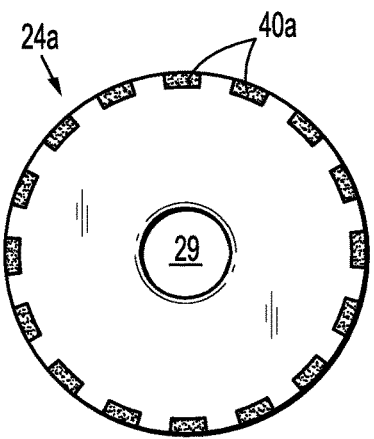
FIG. 1C  FIG. 2A
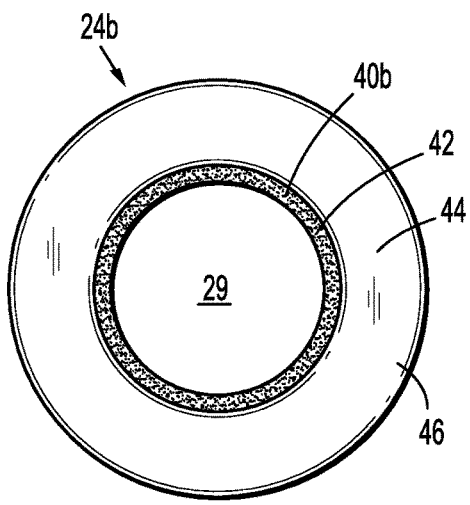
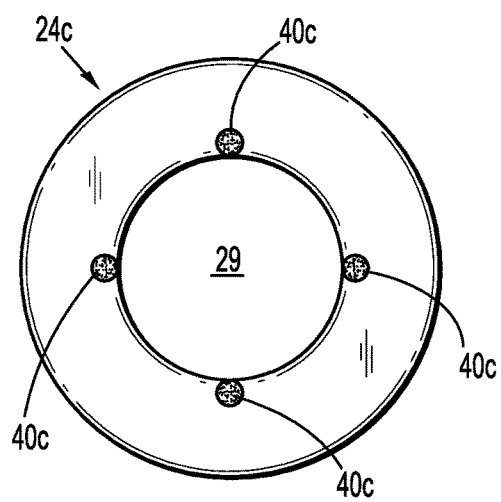
FIG. 2B  FIG. 2C
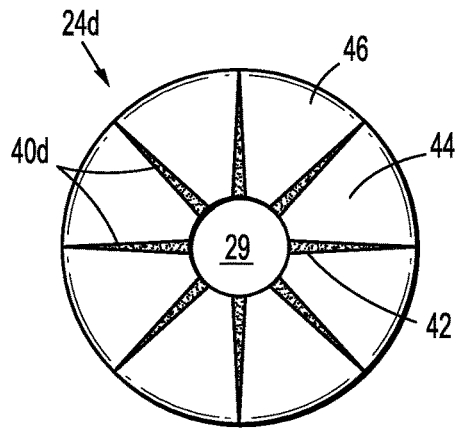
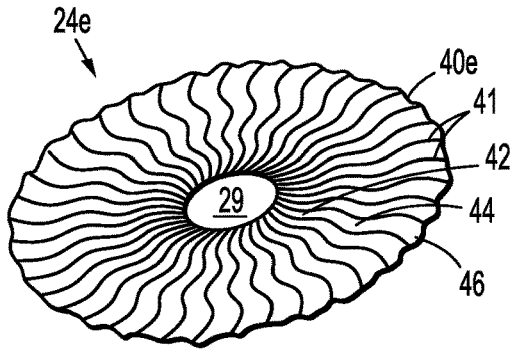
FIG. 2D  FIG. 2E

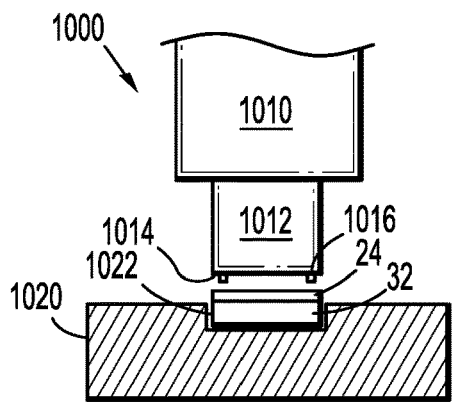
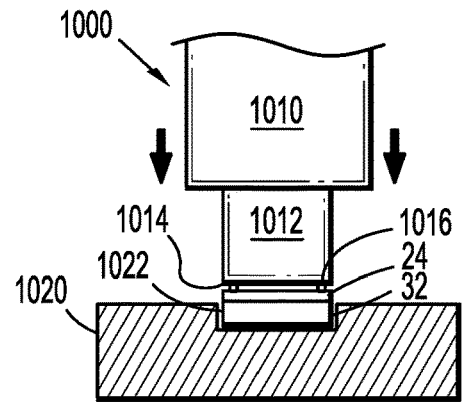
FIG. 3A  FIG. 3B
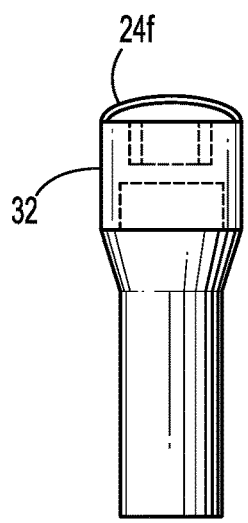
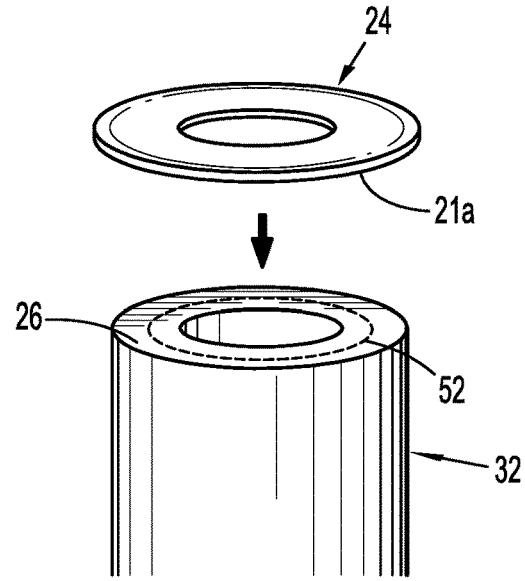
FIG. 4  FIG. 5A
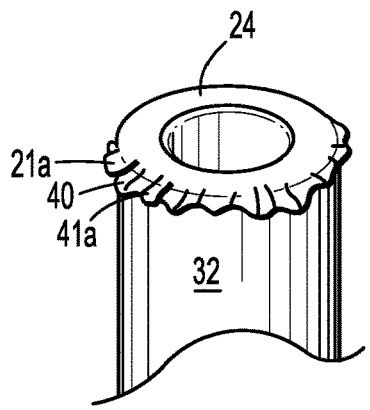
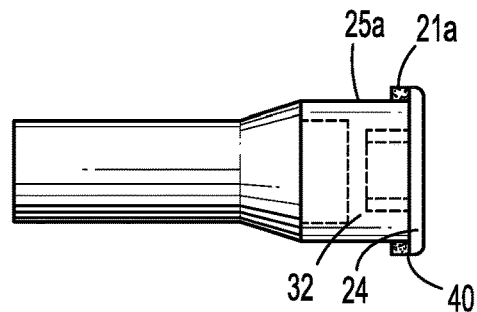
FIG. 5C  FIG. 5B

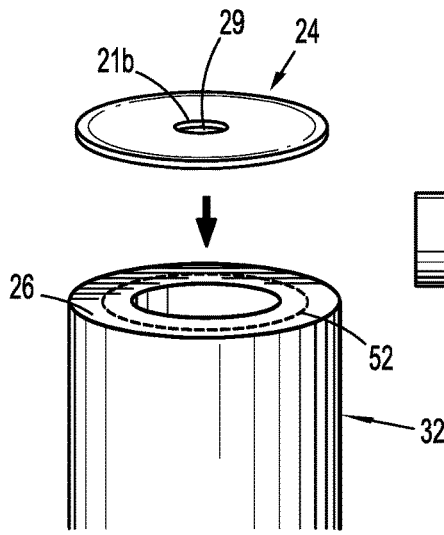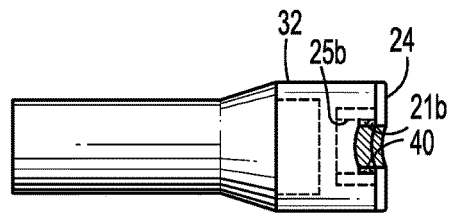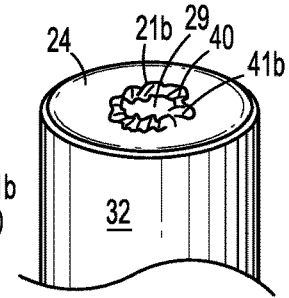
FIG. 6A  FIG. 6B  FIG. 6C
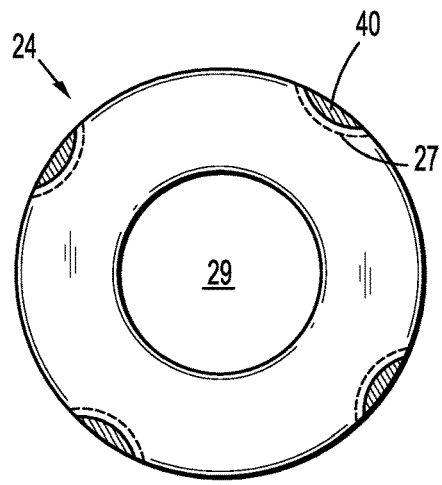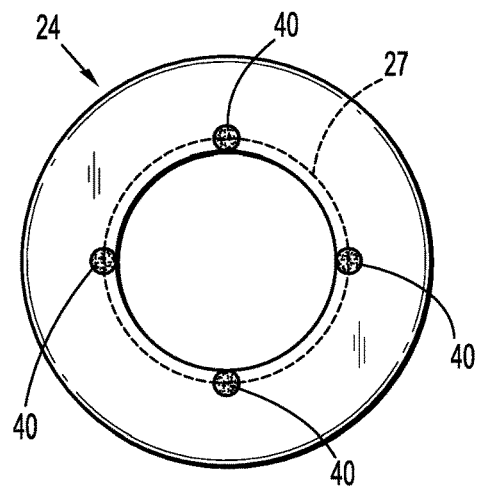
FIG. 7A  FIG. 7B
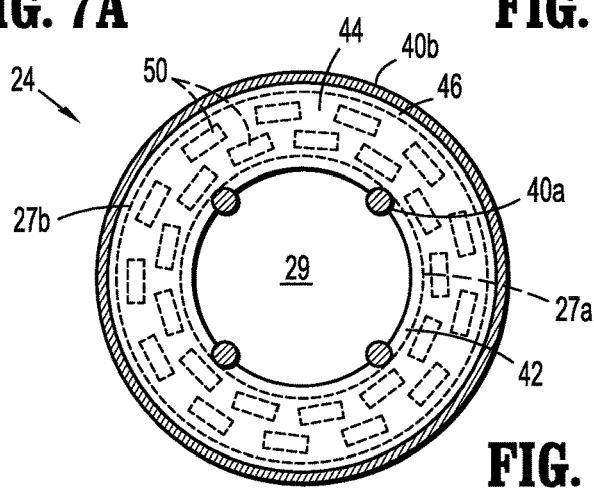
FIG. 7C

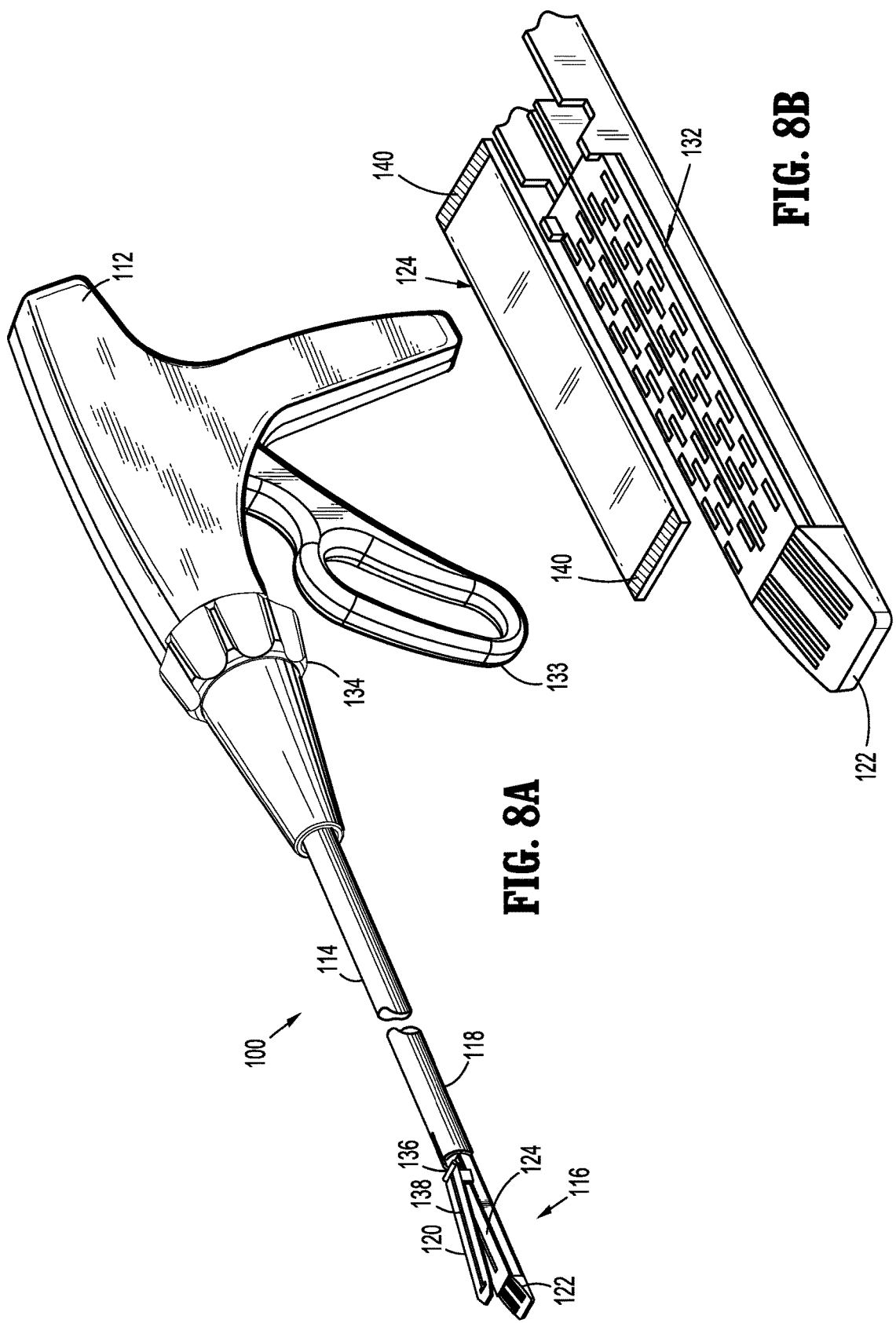

SURGICAL STAPLING APPARATUS INCLUDING RELEASABLE SURGICAL BUTTRESS

CROSS-REFERENCE TO RELATED APPLICATIONS

The present application is a Divisional Application which claims the benefit of and priority to U.S. patent application Ser. No. 13/325,481, filed on Dec. 14, 2011, the entire disclosure of which is hereby incorporated by reference herein.

BACKGROUND

Technical Field

The present disclosure relates to surgical stapling apparatus including surgical buttresses which are releasably attached to the surgical stapling apparatus, and in particular, to surgical stapling apparatus having surgical buttresses having at least a portion with increased rigidity and/or stability.

Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

A number of surgical stapling apparatus rely on secondary materials, such as adhesives or mounting structures (e.g., sutures) to maintain a surgical buttress on the stapling apparatus. The use of additional materials may leave a residue in the body after implantation and/or require increased firing forces as each material must be transected by the knife blade to detach the surgical buttress from the stapling apparatus.

It would be desirable to provide a buttress that may be releasably secured to a surgical stapling apparatus without the need for a secondary material or mounting structure.

Buttress materials that are formed from non-woven or mesh-like materials are known. These materials are relatively flexible and can shift on the surgical stapling apparatus. It may be desirable in at least certain applications to provide a buttress that has a stiffer construction or at least some stiffer portions to facilitate the placement of the buttress on the apparatus, or the placement of the buttress on tissue, or both.

SUMMARY

According to an aspect of the present disclosure, a staple cartridge for use with a surgical stapling apparatus includes a cartridge body including a tissue contacting surface defining a plurality of staple retaining slots, a staple disposed within each staple retaining slot of the cartridge body, and a substantially circular buttress. The buttress includes an inner portion, an outer portion, and a middle portion extending between the inner and outer portions. At least one stiffened region joins the buttress to the tissue contacting surface of the cartridge body. The inner portion, the middle portion, the outer portion, and the at least one stiffened region are all formed from a common material.

The stiffened region may be disposed in any portion of the buttress. In embodiments, at least the outer portion of the buttress includes the stiffened region. In embodiments, at least the inner portion of the buttress includes the stiffened region. In embodiments, the stiffened region includes a plurality of spokes extending radially outward from the inner portion of the buttress to the outer portion of the buttress. In some embodiments, the stiffened region may be disposed radially inward of the staple retaining slots. Alternatively, or additionally, the stiffened region may be disposed radially outward of the staple retaining slots.

The stiffened region may include ruffles. The ruffles may be folds, pleats, undulations, corrugations, creases, ridges, or bends. The stiffened region may be a localized crosslinked region of the buttress. The buttress may include a stiffening agent.

The buttress may include a flange. In embodiments, the outer portion of the buttress includes a terminal flange extending around an outer perimeter of the tissue contacting surface of the cartridge body. In such embodiments, the stiffened region may extend through the terminal flange. The terminal flange may be adjoined to an outer surface of the cartridge body.

The buttress material may include a central opening. The stiffened region may be concentric with the central opening. In embodiments, the inner portion of the buttress may include an interior flange annularly extending into the central opening. In such embodiments, the stiffened region may extend through the interior flange. The interior flange may be adjoined to an inner surface of the cartridge body.

Accordingly to another aspect of the present disclosure, a surgical stapling apparatus includes a tubular body portion, an anvil assembly, a cartridge body, a staple, and a substantially circular buttress. The tubular body portion of the surgical stapling apparatus has a distal end and a shaft with a connection portion, and the anvil assembly includes an anvil plate having staple forming recesses and a shaft connectable with the connection portion. The cartridge body is receivable in the distal end of the tubular body portion and includes a tissue contacting surface defining a plurality of staple retaining slots, the staple retaining slots defining at least two annular rows of staple retaining slots. A staple is disposed within each staple retaining slot of the cartridge body. The buttress includes an inner portion, an outer portion, and a middle portion extending between the inner portion and the outer portion. At least one stiffened region joins the buttress to the tissue contacting surface. The inner portion, the middle portion, the outer portion, and the at least one stiffened region are all formed from a common material.

Accordingly to yet another aspect of the present disclosure, a surgical stapling apparatus includes a tubular body portion, an anvil assembly, a cartridge body, a staple, and a substantially circular buttress. The tubular body portion of the surgical stapling apparatus has a distal end and a shaft with a connection portion, and the anvil assembly includes an anvil plate having staple forming recesses and a shaft connectable with the connection portion. The cartridge body is receivable in the distal end of the tubular body portion and includes a tissue contacting surface defining a plurality of staple retaining slots, the staple retaining slots defining at least two annular rows of staple retaining slots. A staple is disposed within each staple retaining slot of the cartridge body. The buttress includes at least one buttress region and at least one stiffened region formed from a common material.

The stiffened region may be disposed in any portion of the buttress. In embodiments, the stiffened region is disposed about an outer portion of the buttress. In embodiments, the stiffened region is disposed about an inner portion of the buttress. In embodiments, the stiffened region includes a plurality of spokes extending radially outward from an inner portion of the buttress to an outer portion of the buttress. In some embodiments, the stiffened region may be disposed radially inward of the staple retaining slots. Alternatively, or additionally, the stiffened region may be disposed radially outward of the staple retaining slots.

The stiffened region may include ruffles. The stiffened region may be a localized crosslinked region of the buttress. The buttress may include a stiffening agent.

The buttress may include a flange. In embodiments, the buttress includes a terminal flange extending around an outer perimeter of the tissue contacting surface of the cartridge body. In such embodiments, the stiffened region may extend through the terminal flange. The terminal flange may be adjoined to an outer surface of the cartridge body.

The buttress material may include a central opening. The stiffened region may be concentric with the central opening. In embodiments, the buttress may include an interior flange annularly extending into the central opening. In such embodiments, the stiffened region may extend through the interior flange. The interior flange may be adjoined to an inner surface of the cartridge body.

According to another aspect of the present disclosure, a surgical stapling apparatus includes a tubular body portion, an anvil assembly, a cartridge body, a staple, and a substantially circular buttress. The tubular body portion of the surgical stapling apparatus has a distal end and a shaft with a connection portion, and the anvil assembly includes an anvil plate having staple forming recesses and a shaft connectable with the connection portion. The cartridge body is receivable in the distal end of the tubular body portion and includes a tissue contacting surface defining a plurality of staple retaining slots, the staple retaining slots defining at least two annular rows of staple retaining slots. A staple is disposed within each staple retaining slot of the cartridge body. The buttress includes at least one buttress material and at least one stiffened region. The stiffened region is formed by adding a stiffening agent to the buttress material, the stiffening agent being a sugar, a salt, a starch, a hydrogel, a degradable polymer, or combinations thereof.

For example, sugars may include tahalose, sucrose, galatose, and glucose; salts may include sodium chloride, potassium chloride, and sodium phosphate; hydrogels may include degradable polyethylene glycol or poly(2-hydroxyethyl methacrylate); and degradable polymers may include poloxamers or polyhydroxy acids. In embodiments, the polyhydroxy acids are glycolide, lactide, trimethylene carbonate, p-dioxanone, c-caprolactone, or combinations thereof. The stiffening agent may be coated on the buttress and/or impregnated therein.

BRIEF DESCRIPTION OF THE DRAWINGS

Embodiments of the presently disclosed surgical stapling apparatus and surgical buttress are described herein with reference to the accompanying drawings, wherein:

FIG. 1C is a top view of the surgical buttress depicted in FIG. 1B, illustrating its attachment to the surgical stapling apparatus of FIG. 1A;

FIGS. 2A-2D are top views of surgical buttresses in accordance with other embodiments of the present disclosure;

FIG. 2E is a perspective view of a surgical buttress in accordance with an embodiment of the present disclosure;

FIGS. 3A and 3B are cross-sectional views of a staple cartridge of the surgical stapling apparatus and a surgical buttress in accordance with an exemplary process of forming the stiffened regions in accordance with an embodiment of the present disclosure;

FIG. 4 is a schematic side view of a staple cartridge assembly and surgical buttress in accordance with an embodiment of the present disclosure;

FIG. 5A is a perspective view, with parts separated, of a staple cartridge assembly and surgical buttress in accordance with an embodiment of the present disclosure;

FIG. 5B is a schematic side view of the surgical buttress of FIG. 5A positioned on the staple cartridge assembly in accordance with an embodiment of the present disclosure;

FIG. 5C is a schematic perspective view of the surgical buttress of FIG. 5A positioned on the staple cartridge assembly in accordance with another embodiment of the present disclosure;

FIG. 6A is a perspective view, with parts separated, of a staple cartridge assembly and surgical buttress in accordance with an embodiment of the present disclosure;

FIG. 6B is a schematic side view of the surgical buttress of FIG. 6A positioned on the staple cartridge assembly in accordance with an embodiment of the present disclosure;

FIG. 6C is a schematic perspective view of the surgical buttress of FIG. 6A positioned on the staple cartridge assembly in accordance with another embodiment of the present disclosure;

FIGS. 7A-7C are top views of surgical buttresses, illustrating their attachment to the surgical stapling apparatus of FIG. 1A, in accordance with other embodiments of the present disclosure;

FIG. 8A is a perspective view of an illustrative embodiment of a surgical stapling apparatus in accordance with an embodiment of the present disclosure;

FIG. 8B is a perspective view, with parts separated, of the staple cartridge assembly of the surgical stapling apparatus and of the surgical buttress of FIG. 8A;

DETAILED DESCRIPTION OF THE EMBODIMENTS

Figure 1A:
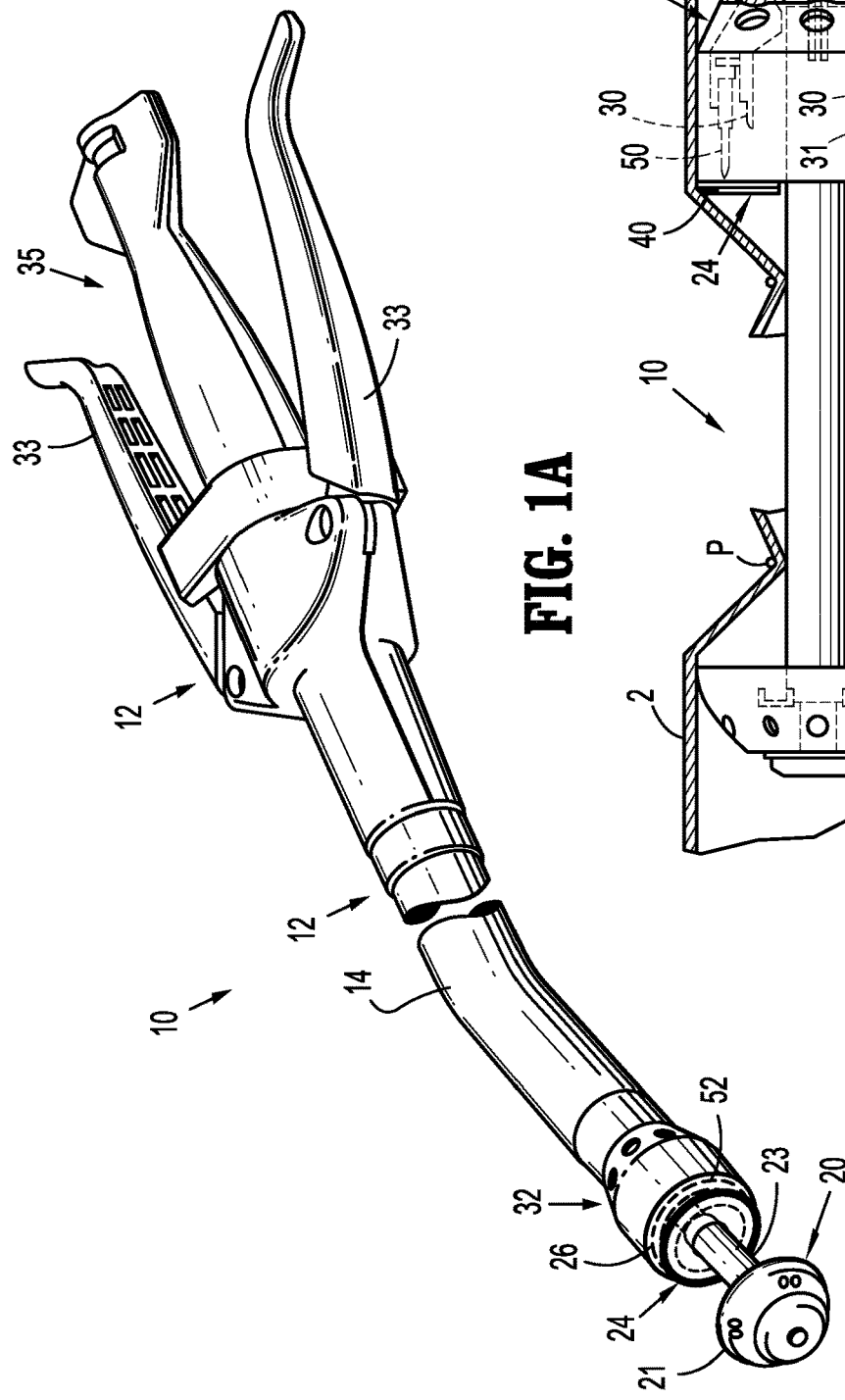
FIG. 1A is a perspective view of an illustrative embodiment of a surgical stapling apparatus and surgical buttress (shown separated from a staple cartridge assembly of the surgical stapling apparatus) in accordance with an embodiment of the present disclosure.

Various exemplary embodiments of the present disclosure are discussed herein below in terms of surgical buttresses for use with surgical stapling apparatus. The surgical buttresses described herein may be used in joining the edges of wound tissue utilizing a surgical stapling apparatus which has at least one surgical buttress mounted thereon. The at least one surgical buttress is joined to the surgical stapling apparatus and includes at least one stiffened region. The at least one stiffened region can adhere, or otherwise be used to connect, the surgical buttress to the surgical stapling apparatus. In embodiments, actuation of a knife provides a force that impinges against the surgical buttress and displaces the buttress by a sufficient amount to weaken or break the bond created by the stiffened region between the surgical buttress and the surgical stapling apparatus, thereby releasing the surgical buttress therefrom before substantial cutting of the buttress material. In other embodiments, cutting of the surgical buttress by the knife blade releases a portion of the surgical buttress that is free of the stiffened region. Thus, the present disclosure describes surgical buttresses, surgical stapling apparatus supporting said surgical buttresses, and methods and mechanisms for using the same.

It should be understood that a variety of surgical stapling apparatus may be utilized with a surgical buttress of the present disclosure. For example, circular stapler configurations may be utilized, such as, for example those including end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference), and linear stapler configurations, such as, for example those including Duet TRS™ reloads and staplers with Tri-Staple™ technology, available through Covidien, which maintain a principal place of business at 555 Long Wharf Drive, North Haven, Conn. 06511, and transverse anastomosis staplers, such as, for example, EEA™ instruments, CEEA™ instruments, GIA™ instruments, EndoGIA™ instruments, and TA™ instruments, also available through Covidien. It should also be appreciated that the principles of the present disclosure are equally applicable to surgical staplers having alternate configurations, such as, for example, laparoscopic staplers (see, e.g., commonly owned U.S. Pat. Nos. 6,330,965 and 6,241,139, each entitled "Surgical Stapling Apparatus," the entire contents of each of which being incorporated herein by this reference) and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Figure 1B:
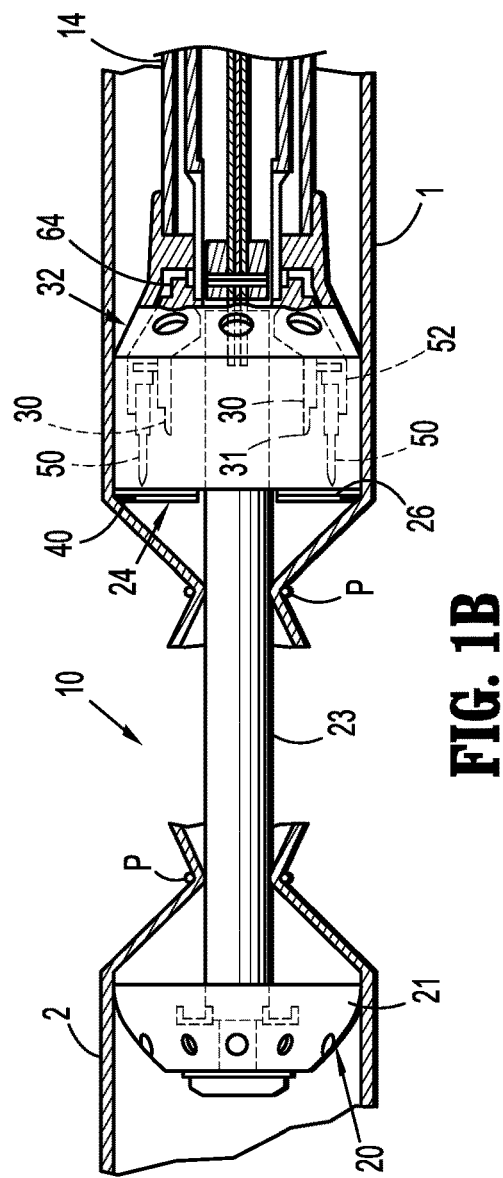
FIG. 1B is a cross-sectional view of a portion of the surgical stapling apparatus of FIG. 1A including a surgical buttress positioned within an intestinal area.

Referring now to FIGS. 1A and 1B, there is disclosed an exemplary surgical stapling apparatus or surgical stapler 10 for use in stapling tissue and applying a buttress material or surgical buttress to the tissue. Surgical stapling apparatus 10 generally includes a handle assembly 12 having at least one pivotable actuating handle member 33, and an advancing member 35. Extending from handle member 12, there is provided a tubular body portion 14 which may be constructed so as to have a curved shape along its length. Body portion 14 terminates in a staple cartridge assembly 32 which includes an annular array of staple retaining slots 52 having a staple 50 disposed in each one of staple retaining slots 52. Positioned distally of staple cartridge assembly 32 there is provided an anvil assembly 20 including an anvil member 21 and a shaft 23 operatively associated therewith for removably connecting anvil assembly 20 to a distal end portion of stapling apparatus 10.

Staple cartridge assembly 32 may be fixedly connected to the distal end of tubular body portion 14 or may be configured to concentrically fit within the distal end of tubular body portion 14. Typically, staple cartridge assembly 32 includes a staple pusher 64 including a proximal portion having a generally frusto-conical shape and a distal portion defining two concentric rings of peripherally spaced fingers (not shown), each one of which is received within a respective staple retaining slot 52.

A knife 30, substantially in the form of an open cup with the rim thereof defining a knife blade 31, is disposed within staple cartridge assembly 32 and mounted to a distal surface of a staple pusher 64. The knife 30 is disposed radially inward of the annular arrays of staples 50. Accordingly, in use, as the staple pusher 64 is advanced, the knife 30 is also advanced axially outward.

Reference may be made to commonly owned U.S. Pat. No. 5,915,616 to Viola et al., referenced above, for a detailed discussion of the construction and operation of an annular stapling device, the disclosure of which is hereby incorporated by reference herein.

A surgical buttress 24 is releasably attached to the staple cartridge assembly 32 by at least one stiffened region 40 that bonds the surgical buttress 24 to a tissue contacting/facing surface of staple cartridge assembly 32. It should be understood that while the surgical buttress 24 is described herein as being associated with the staple cartridge assembly 32, the surgical buttress 24 may, alternatively or additionally, be associated with the anvil assembly 20. Surgical buttress 24 is provided to reinforce and seal staple lines applied to tissue by surgical stapling apparatus 10. Surgical buttress 24 may be configured into any shape, size, or dimension suitable to fit any surgical stapling, fastening, or firing apparatus.

Surgical buttress 24 is fabricated from a biocompatible material which is a bioabsorbable or non-absorbable, natural or synthetic material. It should of course be understood that any combination of natural, synthetic, bioabsorbable, and non-bioabsorbable materials may be used to form the surgical buttress. In embodiments, the entire surgical buttress 24, or portions thereof, may be fabricated from the same material, or combination of materials that is homogeneous throughout the surgical buttress 24. In other embodiments, the surgical buttress 24 may be formed of different materials.

The surgical buttress 24 may be porous, non-porous, or combinations thereof. It is also envisioned that surgical buttress 24 described herein may contain a plurality of layers in which any combination of non-porous and porous layers may be configured as discussed further below. For example, surgical buttress may be formed to include multiple non-porous layers and porous layers that are stacked in an alternating manner. In another example, surgical buttress may be formed in a "sandwich-like" manner wherein the outer layers of the surgical buttress include porous layers and the inner layers are non-porous layers. It is further envisioned that non-porous and porous layers may be positioned in any order relative to the tissue contacting surfaces of the staple cartridge/anvil assembly. Examples of multi-layered surgical buttresses are disclosed in U.S. Patent Application Publication No. 2009/0001122 filed Jun. 27, 2007, entitled "Buttress and Surgical Stapling Apparatus," the entire disclosure of which is incorporated by reference herein.

Some non-limiting examples of materials from which non-porous and/or porous layers of surgical buttress 24 may be made include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends, and combinations thereof.

In embodiments, natural biological polymers are used in forming a non-porous layer of the surgical buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce a non-porous layer of the surgical buttress.

In embodiments, collagen of human and/or animal origin, e.g., type I porcine or bovine collagen, type I human collagen or type III human collagen, may be used to form a non-porous layer of the surgical buttress. In embodiments, a non-porous layer of the surgical buttress according to the present disclosure is made of collagen which is oxidized or a mixture in any proportions of non-oxidized and oxidized collagens.

The use of non-porous layer(s) in the surgical buttress may enhance the ability of the surgical buttress to resist tears and perforations during the manufacturing, shipping, handling, and stapling processes. Also, the use of a non-porous layer in the surgical buttress may also retard or prevent tissue ingrowth from surrounding tissues thereby acting as an adhesion barrier and preventing the formation of unwanted scar tissue. Thus, in embodiments, the non-porous layer(s) of the surgical buttress may possess anti-adhesion properties.

A non-porous layer of the surgical buttress may be formed using techniques within the purview of those skilled in the art, such as casting, molding, and the like.

Any of the porous layers of the surgical buttress may have openings or pores over at least a portion of a surface thereof. As described in more detail below, suitable materials for forming a porous layer include, but are not limited to, fibrous structures (e.g., knitted structures, woven structures, non-woven structures, etc.) and/or foams (e.g., open or closed cell foams). In embodiments, the pores may be in sufficient number and size so as to interconnect across the entire thickness of the porous layer. Woven fabrics, knitted fabrics, and open cell foam are illustrative examples of structures in which the pores can be in sufficient number and size so as to interconnect across the entire thickness of the porous layer. In embodiments, the pores may not interconnect across the entire thickness of the porous layer, but rather may be present at a portion thereof. Thus, in some embodiments, pores may be located on a portion of the porous layer, with other portions of the porous layer having a non-porous texture. Those skilled in the art reading the present disclosure will envision a variety of pore distribution patterns and configurations for the porous layer. Closed cell foam or fused non-woven materials are illustrative examples of structures in which the pores may not interconnect across the entire thickness of the porous layer.

Where a porous layer of the surgical buttress is fibrous, the fibers may be filaments or threads suitable for knitting or weaving or may be staple fibers, such as those frequently used for preparing non-woven materials. Suitable techniques for making fibrous structures are within the purview of those skilled in the art. The buttress material may be made using non-woven processes, including processes disclosed in U.S. patent application Ser. No. 13/293,215, filed Nov. 10, 2011, and entitled Hydrophilic Medical Devices, the disclosure of which is hereby incorporated by reference herein.

Where a porous layer of the surgical buttress is a foam, the porous layer may be formed using any method suitable to forming a foam or sponge including, but not limited to, the lyophilization or freeze-drying of a composition. Suitable techniques for making foams are within the purview of those skilled in the art.

The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In embodiments, a porous layer of the surgical buttress may be made from denatured collagen or collagen which has at least partially lost its helical structure through heating or any other method. The term "denatured collagen" means collagen which has lost its helical structure. The collagen used for the porous layer as described herein may be native collagen or atellocollagen. The collagen may have been previously chemically modified by oxidation, methylation, succinylation, ethylation, or any other known process.

The porous layer(s) may enhance the ability of the surgical buttress to absorb fluid, reduce bleeding, and seal the wound. Also, the porous layer(s) may allow for tissue ingrowth to fix the surgical buttress in place.

As illustrated in the current embodiment, and shown in FIGS. 1B and 1C, surgical buttress 24 includes a radially inner portion 42 defining an aperture 29 to receive shaft 23 of anvil assembly 20, a radially outer portion 46, and a radially middle portion 44 extending between the inner portion 42 and the outer portion 46. Stiffened region 40 is provided in at least a portion of the surgical buttress 24 and is configured to reduce shifting of the buttress or a portion of the buttress in relation to the staple retaining slots 52. The stiffened region 40 may be configured to releasably attach the surgical buttress 24 to the staple cartridge assembly 32.

For example, stiffened region 40 of surgical buttress 24 releasably attaches the staple cartridge assembly 32 in a manner which allows the surgical buttress 24 to be removed or released from the staple cartridge assembly 32 upon actuation of the knife 30. Accordingly, the stiffened region 40 is formed with a bond strength that is strong enough to hold the buttress 24 onto the staple cartridge assembly 32, but is weak enough to break free of the staple cartridge assembly 32 when the knife 30 impacts or penetrates the surgical buttress 24 to facilitate the release of the stiffened region 40 from the tissue contact surface 23 and thus, the surgical buttress 24 upon firing of surgical stapling apparatus 10.

As illustrated, stiffened region 40 is provided in the outer portion 46 of the surgical buttress 24 and bonds the surgical buttress 24 to the inwardly facing or tissue contacting surface 26 of the staple cartridge assembly 32. While the stiffened region 40 is shown as continuously extending around the outer portion 46 of the surgical buttress 24, it should be understood that stiffened region 40 may be discontinuous and include a plurality of stiffened regions 40a attaching the surgical buttress 24a to the surgical stapling apparatus 10, such as in the configuration illustrated in FIG. 2A, for example. In embodiments, the stiffened region 40, 40a may be disposed radially outward of the staple retaining slots 52 (FIGS. 1A and 1B).

Other configurations of the stiffened region 40 may be utilized to retain the surgical buttress 24 on the staple cartridge assembly 32. A stiffened region may be provided in other portions of a surgical buttress, such as, for example, in the inner portion as shown in FIG. 2B. The buttress shown in FIG. 2B can be part of any of the embodiments disclosed herein. In particular, FIG. 2B illustrates a stiffened region 40b extending continuously around an inner portion 42 of surgical buttress 24b. In other embodiments, a stiffened region 40c may be discontinuous as illustrated in FIG. 2C, for example. The buttress shown in FIG. 2C can be part of any of the embodiments disclosed herein. While stiffened region 40c is illustrated as a plurality of circular regions, stiffened region 40c may be formed of any number of suitably shaped and sized regions. In embodiments, the stiffened region 40b, 40c may be disposed radially inward of the staple retaining slots 52 (FIGS. 1A and 1B).

FIG. 2D illustrates a stiffened region 40d including a plurality of spokes extending radially outward from the inner portion 42 to the outer portion 46 of the surgical buttress 24d. The buttress shown in FIG. 2D can be part of any of the embodiments disclosed herein. While the spokes of the stiffened region 40d are illustrated as tapering from the inner portion 42 to the outer portion 46 of the surgical buttress 24, it should be understood that the spokes of the stiffened region 40d may taper from the outer portion 46 to the inner portion 42 of the surgical buttress 24, or be of uniform or changing width from the outer portion 46 to the inner portion 42.

FIG. 2E illustrates a surgical buttress 24e in which the stiffened region 40e extends throughout the inner, outer, and middle portions 42, 44, 46 thereof to form ruffles 41. The buttress shown in FIG. 2E can be part of any of the embodiments disclosed herein. In such embodiments, the ruffles 41 of the stiffened region 40e may be folds, pleats, undulations, corrugations, creases, ridges, bends, or include other fluctuations in the surface of the surgical buttress 24e to provide radial stability to the surgical buttress 24e relative to the staple cartridge assembly 32.

It is envisioned that other configurations, as well as combinations of the embodiments described above, may be utilized to form the stiffened region of a surgical buttress. For example, a surgical buttress may include a stiffened region in both the inner and outer portions of the surgical buttress, or may include ruffles in only a portion thereof. Other configurations will be readily apparent to those skilled in the art. It is envisioned that the number of stiffened regions, stiffened region size, positioning, and spacing can be varied to optimize the attachment of the surgical buttress to the surgical stapling apparatus, as well as to minimize the detachment force required during firing.

The stiffened regions may be formed by applying pressure and/or heat to compress the buttress, or a portion thereof. The pressure and heat may be used to join a surgical buttress to a surgical stapling apparatus, or may be applied during a manufacturing process prior to affixing of the surgical buttress to the surgical stapling apparatus. In embodiments, stiffened regions may be formed by melt pressing, heat staking, and the like. In embodiments in which a fibrous woven or non-woven buttress material is utilized, heat staking the fibers of the surgical buttress will cause the fibers to substantially coalesce or bond to create stiffened regions in the desired portions of the surgical buttress.

As illustrated in FIGS. 3A and 3B, a heat staking apparatus 1000, or the like, is illustrated for attaching a surgical buttress 24 to a staple cartridge assembly 32. The staple cartridge assembly 32 and surgical buttress 24 are placed within a retaining channel 1022 of base 1020 of heat staking apparatus 1000. Heat staking apparatus 1000 includes a compression device 1010 operably connected to a generator (not shown) for activating at least one heating element as is known in the art such that when a die plate 1012 contacts the surgical buttress 24 with a desired amount of pressure, a combination of the desired amount of pressure and/or thermal energy from the compression device 1010 joins the surgical buttress 24 to the staple cartridge assembly 32, forming stiffening region 40. Die 1012 may define a patterned surface 1014 including projections 1016 for forming individual stiffened regions 40 on the surgical buttress 24. Projections 1016 provide small contact surfaces so that the energy delivered by the compression device 1010 is concentrated over a small area. The projections are positioned to form stiffened region 40 and, as described above, may be any shape and size depending on the desired configuration.

In embodiments, the die plate 1012 may assume a concave shape so that the surgical buttress 24f, as shown in FIG. 4, may be heat pressed into a dome shape over staple cartridge assembly 32 to provide structural rigidity to the surgical buttress 24f.

In other embodiments, the stiffened regions may be formed by coating or impregnating the buttress material with a stiffening agent. The stiffening agent is biocompatible and may be dissolvable and/or degradable in vivo. Stiffening agents include, for example: sugars such as tehalose, sucrose, galatose, and glucose; salts such as sodium chloride, potassium chloride, and sodium phosphate; hydrogels such as degradable polyethylene glycol (PEG) or poly(2-hydroxyethyl methacrylate) (pHEMA); and degradable polymer coatings such as those including poloxamers as well as polyhydroxy acids prepared from lactone monomers such as glycolide, lactide, trimethylene carbonate, p-dioxanone, c-caprolactone, and combinations thereof. In some embodiments, the degradable polymer coating may include a copolymer of glycolic acid and trimethylene carbonate. In embodiments, the degradable polymer coating may include a copolymer of 1-lactide and glycolide, and in some embodiments, the coating may include from about 70% 1-lactide and about 30% glycolide. In embodiments, the coating may include a copolymer of glycolide and e-caprolactone, and in some embodiments, from about 15% glycolide and about 85% e-caprolactone. The stiffening agent may impart rigidity to the surgical buttress for several minutes after contact with body fluids after insertion of the surgical stapling apparatus into the body cavity, leaving the buttress material supple after implantation.

Referring again to FIG. 1A and 1B, surgical stapling apparatus 10 and detachable anvil assembly 20 are used in an anastomosis procedure to effect joining of intestinal sections 1 and 2. The anastomosis procedure is typically performed using minimally invasive surgical techniques including laparoscopic means and instrumentation. At the point in the procedure shown in FIG. 1B, a diseased intestinal section has been previously removed, anvil assembly 20 has been applied to the operative site either through a surgical incision or transanally and positioned within intestinal section 2, and tubular body portion 14 of surgical stapling apparatus 10 has been inserted transanally into intestinal section 1. Intestinal sections 1 and 2 are also shown temporarily secured about their respective components (e.g., shaft 23 of anvil assembly 20, and the distal end of tubular body portion 14) by conventional means such as a purse string suture "P".

Thereafter, the clinician maneuvers anvil assembly 20 until the proximal end of shaft 23 is inserted into the distal end of tubular body portion 14 of surgical stapling apparatus 10, wherein a mounting structure within the distal end of tubular body portion 14 engages shaft 23 to effect the mounting. Anvil assembly 20 and tubular body portion 14 are then approximated to approximate intestinal sections 1, 2. Surgical stapling apparatus 10 is then fired. The staples 50 are fired, effecting stapling of intestinal sections 1, 2 to one another. The force of the knife 30 being fired breaks the bonds between the surgical buttress 24 and the staple cartridge assembly 32 created by stiffened region 40 thereby releasing the surgical buttress 24 from the staple cartridge assembly 32, and cutting the portion of tissue and surgical buttress 24 disposed radially inward of the knife 30, to complete the anastomosis.

Referring now to FIGS. 5A-6C, the surgical buttress may include an outer and/or inner flange. As shown in FIG. 5A-5C, surgical buttress 24 may include a terminal flange 21a extending around an outer perimeter of the tissue contacting surface 23 of the staple cartridge assembly 32. In embodiments, as shown in FIG. 5B, terminal flange 21a may be secured to a side surface 25a of the staple cartridge assembly 32. Terminal flange 21a of surgical buttress 24 may be joined to an outer side surface 25a of the staple cartridge assembly 32 via stiffened region 40 by melt pressing, heat staking, and the like, as described above. Alternatively, as shown in FIG. 5C, terminal flange 21a may extend outwardly from the staple cartridge assembly 32 such that the stiffened region 40, shown as ruffles 41a, provide stability around the edges of the staple cartridge assembly 32. The flange and/or ruffled portion disclosed herein can be included in any of the embodiments disclosed herein. Furthermore, the flange and/or the ruffled portion can be provided as a resilient material that resiliently engages the stapling apparatus or instrument. Furthermore, the flange and/or ruffled portion can be provided as a material having a desirable frictional characteristic for frictionally engaging the stapling apparatus or instrument.

As shown in FIG. 6A-6C, surgical buttress 24 may include an interior flange 21b annularly extending into aperture 29 of surgical buttress 24. In embodiments, as shown in FIG. 6B, interior flange 21b may be joined to an inner side surface 25b of the staple cartridge assembly 32 via stiffened region 40. Alternatively, as shown in FIG. 6C, internal flange 21b may extend inwardly into aperture 29 such that the stiffened region 40, shown as ruffles 41b, provide stability around the inner edges of the staple cartridge assembly 32. The interior flange and/or ruffled portion disclosed herein can be included in any of the embodiments disclosed herein. Furthermore, the flange and/or ruffled portion can be provided as a resilient material that resiliently engages the stapling apparatus or instrument. Furthermore, the flange and/or the ruffled portion can be provided as a material having a desirable frictional characteristic for frictionally engaging the stapling apparatus or instrument.

A surgical buttress of the present disclosure may include perforations or cut zones around and/or through the stiffened region to allow the surgical buttress to release by breaking the perforations or cut zones when a specified amount of force is applied thereto. Such perforations or cut zones can be included in any of the embodiments disclosed herein. Perforations or cut zones allow for repeatable separation of the surgical buttress from the staple cartridge and/or anvil assembly, and would allow for stronger attachment of a surgical buttress by the stiffened region while also reducing the risk of movement or detachment prior to firing of the surgical stapling apparatus. As detachment is effected by breaking the perforations, knife cutting of the surgical buttress is not required for buttress release and thus, increased firing forces may not be required.

Perforations may be formed by placing a surgical buttress between two knife blades with the spacing between the blades corresponding to a percentage of the average thickness of the surgical buttress. The knife blade spacing could be tailored in the range of about 10% to about 100% of the average thickness of the surgical buttress, in embodiments, from about 20% to about 90% of the average thickness, and in some embodiments, about 30% of the average thickness, to ensure that the surgical buttress is well secured during insertion but break away from the stiffened regions upon firing of the surgical stapling apparatus.

As illustrated in FIG. 7A, in one embodiment, a surgical buttress 24 includes at least one stiffened region 40 disposed radially outward of the annular row of staples 50 (FIG. 1B) and perforations 27 extending around the periphery of the stiffened regions 40. Upon firing the surgical stapling apparatus (FIGS. 1A and 1B), the knife 30 (FIG. 1B) disposed within the staple cartridge assembly 32 (FIG. 1B) will impact or penetrate the surgical buttress 24 and allow the portions of the surgical buttress 24 to separate from the stiffened regions 40, via perforations 27, and pull apart from the stiffened regions which are adhered to the staple cartridge assembly 32 (FIG. 1B).

In another embodiment, shown in FIG. 7B, a surgical buttress 24 includes at least one stiffened region 40 disposed radially inward of the annular row of staples 50 (FIG. 1B) and perforations 27 extending in a circumferential line through the stiffened regions 40. Upon firing the surgical stapling apparatus (FIGS. 1A and 1B), the knife 30 (FIG. 1B) disposed within the staple cartridge assembly 32 (FIG. 1B) will impact or penetrate the surgical buttress 24 separating a portion of the surgical buttress 24 extending radially outward of the perforations 27 from the portion of the surgical buttress 24.

It is envisioned that other configurations of perforations may be provided within a surgical buttress. For example, FIG. 7C illustrates a surgical buttress including at least one stiffened region 40a disposed radially inward of the annular row of staples 50 (shown in phantom) and at least one stiffened region 40b disposed radially outward of the annular row of staples 50. Perforations 27a and 27b are provided between stiffened regions 40a and 40b. In embodiments, the perforations 27a and 27b form a circumferential perforation line separating a middle portion 44 of the surgical buttress 24 from the inner and outer portions 42, 46, respectively, of the surgical buttress 24 such that the middle portion 44 can be stapled to tissue while the inner and outer portions 42, 46 remains with the staple cartridge assembly 32.

The surgical buttress of the present disclosure may be adapted for use with other surgical stapling apparatus in accordance with the present disclosure, such as the surgical stapling apparatus disclosed in commonly owned U.S. Pat. Nos. 6,330,965 and 6,241,139, the entire contents of which are incorporated by reference herein. For example, surgical stapling apparatus for both laparoscopic and/or endoscopic surgical procedures that include an elongated body and a tool assembly for applying a linear row or rows of staples can have a buttress as disclosed in any of the embodiments hereof. Apparatus for applying a linear row or rows of staples that are arranged for open surgical procedures can also have any of the buttresses disclosed in any of the embodiments discussed herein. Apparatus having a distal end adapted to releasably engage a disposable loading unit can be used, or apparatus having removable and replaceable cartridges can be used, with the surgical buttresses disclosed herein.

As illustrated in FIGS. 8A and 8B, an exemplary surgical stapling apparatus or surgical stapler 100 for use in stapling tissue and applying a buttress material or surgical buttress to the tissue. Surgical stapling apparatus 100 generally includes a handle 112 having an elongate tubular member 114 extending distally from handle 112. A jaw assembly 116 is mounted on a distal end 118 of elongate tubular member 114. Jaw assembly 116 includes a staple clinching anvil jaw member 120 and a receiving jaw member 122 configured to receive a staple cartridge assembly 132. Jaw assembly 116 may be permanently affixed to elongate tubular member 114 or may be detachable and thus replaceable with a new jaw assembly 116. Staple clinching anvil jaw member 120 is movably mounted on distal end 118 of jaw assembly 116 and is movable between an open position spaced apart from staple cartridge jaw member 122 to a closed position substantially adjacent staple cartridge jaw member 122.

Surgical stapling apparatus 100 further includes a trigger 133 movably mounted on handle 112. Actuation of trigger 133 initially operates to move anvil jaw member 120 from the open to the closed position relative to staple cartridge jaw member 122 and subsequently actuates surgical stapling apparatus 100 to apply lines of staples to tissue. In order to properly orient jaw assembly 116 relative to the tissue to be stapled, surgical stapling apparatus 100 is additionally provided with a rotation knob 134 mounted on handle 112. Rotation of rotation knob 134 relative to handle 112 rotates elongate tubular member 114 and jaw assembly 116 relative to handle 112 so as to properly orient jaw assembly 116 relative to the tissue to be stapled.

A driver 136 is provided to move anvil jaw member 120 between the open and closed positions relative to staple cartridge jaw member 122. Driver 136 moves between a longitudinal slot 138 formed in anvil jaw member 120. A knife (not shown) is associated with driver 136 to cut tissue captured between anvil jaw member 120 and staple cartridge jaw member 122 as driver 136 passes through slot 138.

As illustrated in the current embodiment and shown in FIG. 8B, the surgical buttress 124 is releasably attached to the staple cartridge assembly 132 and/or the anvil jaw member 120 by at least one stiffened region 140 that bonds the surgical buttress 124 to the inwardly facing or tissue contacting surface 126 of the staple cartridge 132 and/or the anvil jaw member 120, in a manner similar to the bonds securing surgical buttresses 24 to the staple cartridge assembly 32, as described above.

Figure 9:
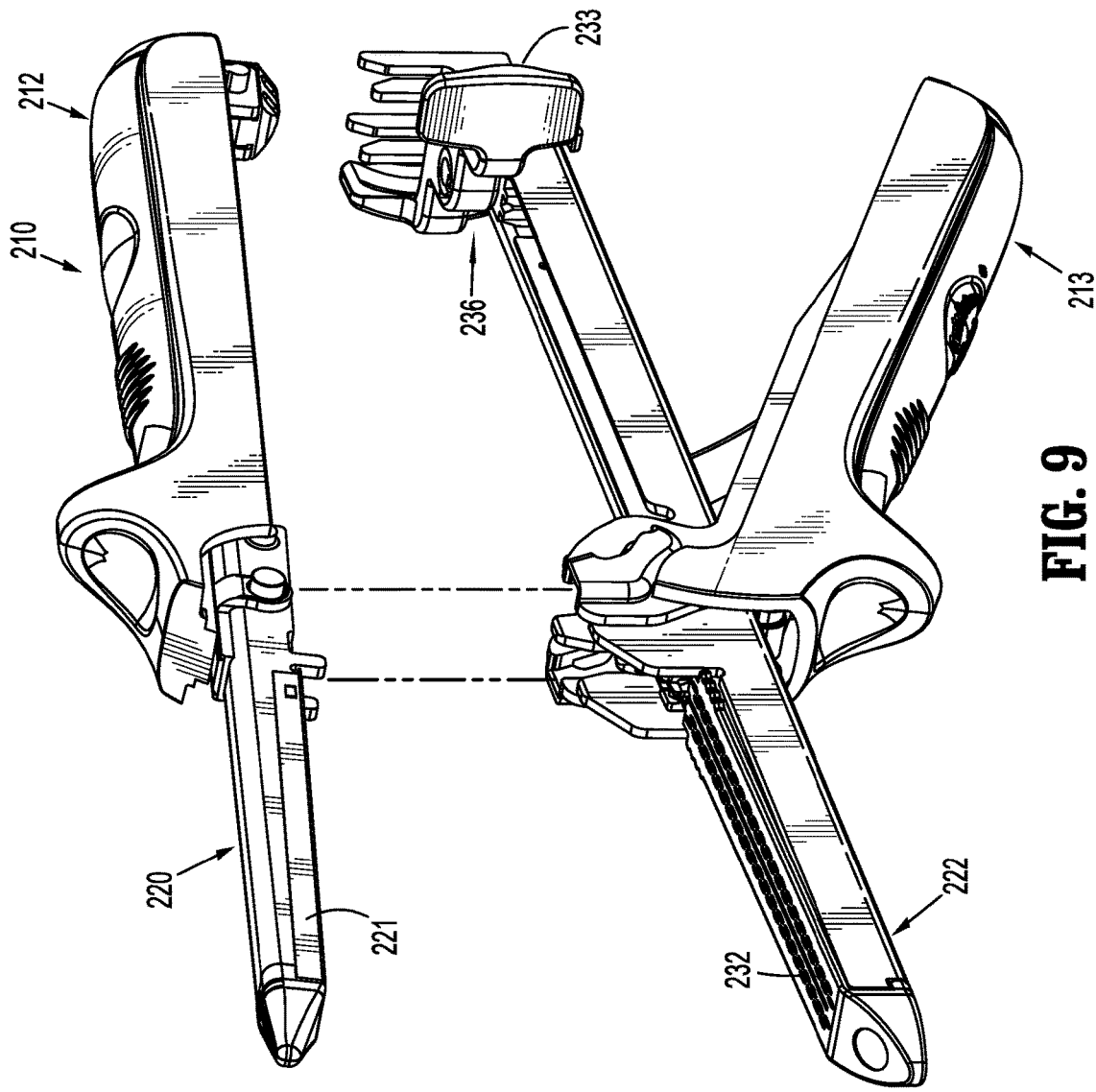
FIG. 9 is a perspective view of another illustrative embodiment of a surgical stapling apparatus for use with a surgical buttress of the present disclosure.

The surgical buttress of the present disclosure, in particular surgical buttress 124, may also be adapted for use with a surgical stapling apparatus, such as that shown and described in U.S. Pat. No. 7,334,717, entitled "Surgical Fastener Applying Apparatus," the entire content of which is incorporated herein by reference. As illustrated in FIG. 9, surgical stapling apparatus 210 includes an anvil receiving section 220 and a cartridge receiving section 222. A surgical buttress (not shown) may be attached to at least one of an anvil 221 coupled to the anvil receiving section 220, a staple cartridge assembly 232 coupled to the cartridge receiving section 222, or both, as discussed above, by at least one stiffened region. The anvil receiving section 220 and the cartridge receiving section 222 are pivotally connected via handles 212, 213 for approximation during use. Following approximation of the anvil receiving section 220 and the cartridge receiving section 222, the surgical stapling apparatus 210 is fired by driving a firing slide 236 distally through the advancement of a firing lever 233. Distal movement of the firing slide 233 causes a plurality of cam bars to engage camming surfaces that interact with a plurality of pushers to expel a plurality of surgical staples (not shown) from the cartridge receiving section 222. The staples are positioned on either side of a track which guides a knife (not shown) during longitudinal movement. The force of the knife being fired breaks the bonds between the surgical buttress and the staple cartridge, for example, created by the stiffened region between the surgical buttress and the staple cartridge, thereby releasing the surgical buttress from the staple cartridge, and severs tissue along a cut-line.

Figure 10:
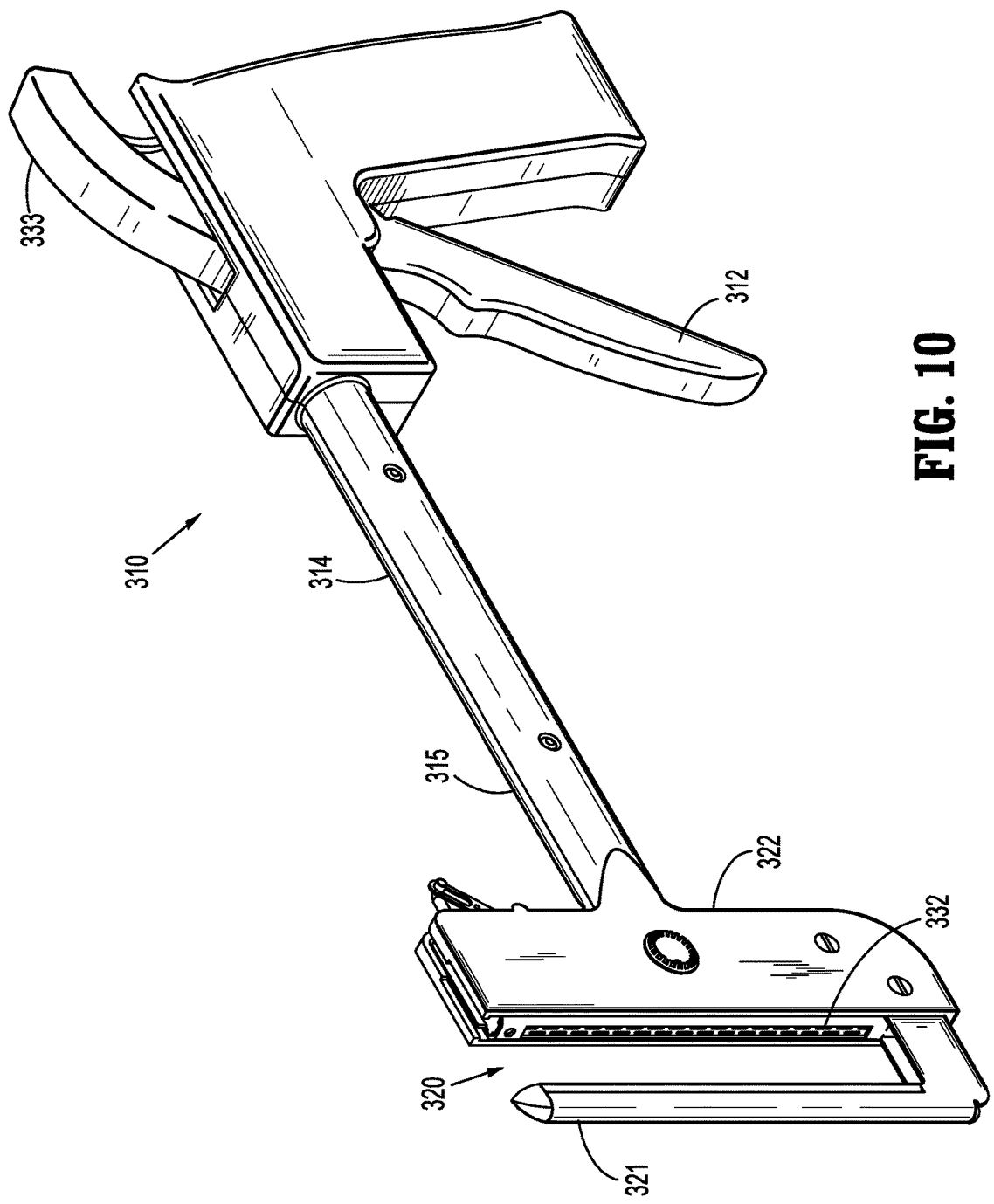
FIG. 10 is a perspective view of yet another illustrative embodiment of a surgical stapling apparatus for use with a surgical buttress of the present disclosure.

The surgical buttress of the present disclosure, in particular surgical buttress 124, may also be adapted for use with a transverse surgical stapling apparatus 310, as illustrated in FIG. 10. An exemplary transverse surgical stapling apparatus is shown and described in U.S. Pat. No. 5,964,394, entitled "Surgical Fastener Applying Device," the entire content of which is incorporated herein by reference. The surgical stapling apparatus 310 includes an approximation lever 333, a movable handle 312, an elongated portion 314 that extends distally from the handle 312, and an arm 322 that extends from a distal end 315 of the elongated portion 314. The surgical stapling apparatus 310 further includes an anvil 321 that is orthogonally affixed to the arm 322, and a cartridge receiver 320 that is operatively coupled to the distal end 315 of the elongated portion 314 for retention of a staple cartridge assembly 332. A surgical buttress (not shown) may be joined to at least one of the anvil 321, staple cartridge assembly 332, or both as discussed above, via a stiffened region.

In embodiments, at least one bioactive agent may be combined with a surgical buttress of the present disclosure. The at least one bioactive agent may be disposed on a surface of the surgical buttress and/or impregnated therein. In these embodiments, the surgical buttress can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the surgical buttress in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be included as a bioactive agent in the surgical buttress of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anticonvulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-viral s; anticoagulants; anticonvulsants; antidepressants; antihistamines; and immunological agents.

Other examples of suitable bioactive agents which may be included include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

In embodiments, a reinforcement member may be positioned within or over a surgical buttress. In embodiments utilizing a multilayered surgical buttress, one or more reinforcement members may be positioned between, within, or at an external surface of a layer of the surgical buttress as are disclosed, for example, in U.S. Patent Application Publication No. 2009/0001122, referenced above.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A staple cartridge assembly for use with a surgical stapling apparatus, the staple cartridge assembly comprising:
   a cartridge body including a proximal end, a distal end, a side surface extending from the distal end and towards the proximal end, and a tissue contacting surface at the distal end defining a plurality of staple retaining slots; and
   a surgical buttress including a buttress body and a flange formed from a common material, the buttress body having an inner terminal radial edge defining an aperture and an outer terminal radial edge, the flange extending from at least one of the inner or outer terminal radial edges of the buttress body, the flange having a stiffened region having ruffles, wherein the stiffened region is formed by increasing rigidity of the flange such that a rigidity of the stiffened region is greater than a rigidity of the buttress body, and wherein the ruffles are secured to the side surface of the cartridge body for maintaining the buttress body of the surgical buttress on the tissue contacting surface of the cartridge body.

2. The staple cartridge assembly according to claim 1, wherein the flange extends from the outer terminal radial edge of the buttress body outwardly beyond an outer perimeter of the tissue contacting surface of the cartridge body.

3. The staple cartridge assembly according to claim 2, wherein the flange is adjoined to the side surface comprising an outer side surface of the cartridge body.

4. The staple cartridge assembly according to claim 1, wherein the flange extends from the inner terminal radial edge of the buttress body and into the aperture of the buttress body, inwardly beyond an inner perimeter of the tissue contacting surface of the cartridge body.

5. The staple cartridge assembly according to claim 4, wherein the flange is adjoined to the side surface comprising an inner side surface of the cartridge body.

6. The staple cartridge assembly according to claim 1, wherein the ruffles are selected from the group consisting of folds, pleats, undulations, corrugations, creases, ridges, and bends.

7. The staple cartridge assembly according to claim 1, wherein the stiffened region is thermally joined to the side surface of the cartridge body.

8. The staple cartridge assembly according to claim 1, wherein the cartridge body includes a knife disposed therein, and the stiffened region of the flange has a bond strength sufficient to hold the surgical buttress to the cartridge body and to break free of the cartridge body when the knife impacts the buttress body.

9. The staple cartridge assembly according to claim 1, wherein the buttress body extends across the tissue contacting surface of the cartridge body, and the flange is disposed radially inwardly or outwardly of the respective inner or outer terminal radial edge of the buttress body.

10. A surgical stapling apparatus, comprising:
    a body portion having a distal end portion;
    an anvil assembly including an anvil plate and a shaft connectable with the distal end portion of the body portion;
    a staple cartridge assembly including a cartridge body receivable in the distal end portion of the body portion and having a tissue contacting surface; and a surgical buttress including a buttress body and a flange formed from a common material, the buttress body having an inner terminal radial edge defining an aperture and an outer terminal radial edge, the flange extending from at least one of the inner or outer terminal radial edges of the buttress body, the flange having a stiffened region having ruffles, wherein the stiffened region is formed by increasing rigidity of the flange such that a rigidity of the stiffened region is greater than a rigidity of the buttress body, and wherein the ruffles are secured to a side surface, extending in a direction towards the body portion, of the cartridge body for maintaining the buttress body of the surgical buttress on the tissue contacting surface of the cartridge body.

11. The surgical stapling apparatus according to claim 10, wherein the flange extends from the outer terminal radial edge of the buttress body outwardly beyond an outer perimeter of the tissue contacting surface of the cartridge body.

12. The surgical stapling apparatus according to claim 11, wherein the flange is adjoined to the side surface comprising an outer side surface of the cartridge body.

13. The surgical stapling apparatus according to claim 10, wherein the flange extends from the inner terminal radial edge of the buttress body and into the aperture of the surgical buttress, inwardly beyond an inner perimeter of the tissue contacting surface of the cartridge body.

14. The surgical stapling apparatus according to claim 13, wherein the flange is adjoined to the side surface comprising an inner side surface of the cartridge body.

15. The surgical stapling apparatus according to claim 10, wherein the ruffles are selected from the group consisting of folds, pleats, undulations, corrugations, creases, ridges, and bends.

16. The surgical stapling apparatus according to claim 10, wherein the stiffened region is thermally joined to the side surface of the cartridge body.

17. The surgical stapling apparatus according to claim 10, wherein the staple cartridge assembly includes a knife disposed within the cartridge body, and the stiffened region of the flange has a bond strength sufficient to hold the surgical buttress to the cartridge body and to break free of the cartridge body when the knife impacts the buttress body.

18. The surgical stapling apparatus according to claim 10, wherein the buttress body extends across the tissue contacting surface of the cartridge body, and the flange is disposed radially inwardly or outwardly of the respective inner or outer terminal radial edge of the buttress body.

* * * * *